(12) United States Patent
De-Stefani et al.

(10) Patent No.: US 12,611,518 B2
(45) Date of Patent: Apr. 28, 2026

(54) FLOAT-CONTROLLED VALVE ARRAY HAVING REDUNDANTLY ACTING FLOAT BODIES

(71) Applicant: Hamilton Medical AG, Bonaduz (CH)

(72) Inventors: Dino De-Stefani, Chur (CH); Remo Senn, Zizers (CH)

(73) Assignee: Hamilton Medical AG, Bonaduz (CH)

( * ) Notice: Subject to any disclaimer, the term of this patent is extended or adjusted under 35 U.S.C. 154(b) by 629 days.

(21) Appl. No.: 17/925,915

(22) PCT Filed: May 31, 2021

(86) PCT No.: PCT/EP2021/064561
§ 371 (c)(1),
(2) Date: Nov. 17, 2022

(87) PCT Pub. No.: WO2021/245030
PCT Pub. Date: Dec. 9, 2021

(65) Prior Publication Data
US 2023/0173219 A1     Jun. 8, 2023

(30) Foreign Application Priority Data

Jun. 4, 2020    (DE) ..................... 10 2020 114 921.2

(51) Int. Cl.
*A61M 16/16*          (2006.01)
(52) U.S. Cl.
CPC ........ *A61M 16/167* (2014.02); *A61M 16/168* (2014.02)
(58) Field of Classification Search
CPC ........................... A61M 16/167; A61M 16/168
(Continued)

(56) References Cited

U.S. PATENT DOCUMENTS

| | | | | |
|---|---|---|---|---|
| 1,258,938 A | * | 3/1918 | Pape .................. | H05B 41/2827 137/433 |
| 3,142,310 A | * | 7/1964 | Feldermann .............. | F24F 6/04 137/434 |

(Continued)

FOREIGN PATENT DOCUMENTS

| | | |
|---|---|---|
| DE | 535721 C | 10/1931 |
| DE | 640283 C | 12/1936 |

(Continued)

OTHER PUBLICATIONS

International Preliminary Report on Patentability for corresponding PCT/EP2021/064561 mailed Dec. 6, 2022, 8 pgs.

(Continued)

*Primary Examiner* — Charles S Bushey
(74) *Attorney, Agent, or Firm* — Rankin, Hill & Clark LLP

(57)          ABSTRACT

A float-controlled valve array including a valve assembly having a conduit, a valve seat formation through which the conduit passes, and a valve body formation which is movable between a closed position in which the conduit is closed and an open position in which a flow through the conduit is possible; the valve array further including a first and a second float body having a first and a second buoyancy volume portion, respectively, wherein the first and the second float bodies are articulated pivotally on a first and a second joint, respectively, so that during specified normal operation, each float body is movable along a buoyancy axis between a lowered position and a buoyant position, and wherein the first float body and the second float body are each coupled to the valve body formation in such a way that the valve body formation is in the closed position when at least one of the float bodies is in the buoyant position, and is in the open position when both float bodies are in the lowered position; the buoyancy volume portions of the two (Continued)

float bodies are mutually spaced apart at a distance orthogonal to the buoyancy axis in the lowered position, wherein at least one joint is located in a body spacing region between the two buoyancy volume portions.

19 Claims, 6 Drawing Sheets

(58) Field of Classification Search
    USPC ............................................................ 261/70
    See application file for complete search history.

(56) References Cited

U.S. PATENT DOCUMENTS

| | | | | |
|---|---|---|---|---|
| 3,985,836 | A | * | 10/1976 | Fischer .................... F02M 5/12 |
| | | | | 137/426 |
| 4,034,026 | A | * | 7/1977 | Miller ..................... F02M 5/12 |
| | | | | 261/DIG. 50 |
| 4,913,140 | A | | 4/1990 | Orec et al. |
| 5,445,143 | A | | 8/1995 | Sims |
| 5,916,489 | A | | 6/1999 | Takeuchi |
| 2003/0030156 | A1 | * | 2/2003 | Fujino ...................... F02M 5/16 |
| | | | | 261/70 |
| 2013/0154133 | A1 | * | 6/2013 | Webster ................ B29C 44/586 |
| | | | | 261/70 |
| 2016/0199614 | A1 | * | 7/2016 | Donnelly ................ F16K 31/26 |
| | | | | 128/203.25 |

FOREIGN PATENT DOCUMENTS

| | | |
|---|---|---|
| EP | 2119466 A1 | 11/2009 |
| JP | S6114272 U | 1/1986 |

OTHER PUBLICATIONS

Google Patents Bibliographic data: JP S6114272(U), Published Jan. 27, 1986, 2 pgs.
German Search Report for corresponding DE 10 2020 114 921.2 mailed Mar. 7, 2021, 8 pgs.
International Search Report for corresponding PCT/EP2021/064561 mailed Sep. 16, 2021, 16 pgs.

* cited by examiner

FLOAT-CONTROLLED VALVE ARRAY HAVING REDUNDANTLY ACTING FLOAT BODIES

This Application claims priority in PCT application PCT/EP2021/064561 filed on May 31, 2021, which claims priority in German Patent Application DE 10 2020 114 921.2 filed on Jun. 4, 2020, which are incorporated by reference herein.

The present invention concerns a float-controlled valve array, in particular for use in humidification devices of respiratory devices for artificial ventilation of humans or animals. The invention further concerns a humidification device with such a valve array.

The float-controlled valve array comprises a valve module with a duct, a valve seat formation penetrated through by the duct, and a valve body formation, where the valve body formation is displaceable relative to the valve seat formation between a closure position, in which the duct is closed through physical abutment of the valve body formation against the valve seat formation, and a passage position, in which the valve body formation is arranged with a separation from the valve seat formation such that flow through the duct is possible. The valve array further comprises a first float body with a first buoyancy volume section and a second float body with a second buoyancy volume section. The first float body is articulated in a swiveling manner at a first joint and the second float body is articulated in a swiveling manner at a second joint. Consequently, in normal operation of the valve array each float body is movable along a buoyancy axis parallel to the gravitational direction between a sinking position and a buoyancy position. The first and the second float body are each coupled with the valve body formation in such a way that the valve body formation is in the closure position if at least one of the float bodies is in the buoyancy position, and is in the passage position if both float bodies are in the sinking position.

BACKGROUND OF THE INVENTION

Such a float-controlled valve array and a humidification device with one are known from U.S. Pat. No. 5,445,143. The first float body of this known valve array serves as a main float body, which should determine definitively the position of the valve body formation relative to the valve seat formation. The second float body serves as a reserve float body, which should take over the tasks of the first float body if the first float body fails. The filling levels and the filling quantities at which the first and the second float body reach their buoyancy position and thereby each ensure a closure of the duct, differ considerably in quantitative terms. The buoyancy volume section of each float body, which by interaction with a fluid quantity ensures or essentially ensures the buoyancy force which is necessary for shifting the associated float body into the buoyancy position, is connected rigidly with a bridge. Each bridge is articulated via a joint at an insert in the filling volume of the container of the humidification device exhibiting the known valve array. Because of the swiveling mobility of the float bodies, the trajectory of their buoyancy volume sections exhibits between the sinking and the buoyancy position not only a movement component along the buoyancy axis, but also, albeit to a lesser extent, orthogonally to it. The two float bodies are arranged either one above the other along the buoyancy axis, then they can differ in size or be equal in size, or the two float bodies are arranged side by size orthogonally to the buoyancy axis, then they have to differ in size so that one acts as main and the other as reserve float body.

A further valve array with a main and a reserve float body is known from EP 2 119 466 A1. Unlike the aforementioned U.S. Pat. No. 5,445,143, here the first and the second float body are each movable in a translatory manner only along the buoyancy axis between the sinking position and the buoyancy position. The translatory mobility makes possible a concentric arrangement of the two float bodies with respect to the buoyancy axis. The outer reserve float body is guided at the housing of the humidification device for movement between its operating positions. The inner main float body is guided at the reserve float body. Therefore through canting of even just one of the float bodies, the entire float body arrangement can be blocked in its movement. For the valve array known from EP 2 119 466 A1 too, it is the case that the filling levels and the filling quantities in the humidification device exhibiting the valve array, which effect a movement of the main and of the reserve float body into the buoyancy position, differ considerably in quantitative terms.

The duct of the valve array is normally a duct through which fluid can flow into a filling volume in which the float bodies are arranged. Thereby in the state of the art, on reaching a filling height which is determined by the structural design and the arrangement of the main float body, the float body is moved into the buoyancy position, whereby the valve body formation closes the duct. If the filling level in the region of the float body decreases, for example through evaporation and transportation away of water vapor, the float body is displaced gravitationally-driven from its buoyancy position back in the direction of the sinking position, whereby the valve body formation lifts from the valve seat formation and fluid can flow in again through the duct into the region of the float body. Consequently, through the valve array the filling quantity of fluid in the region of the float body can be regulated and limited to a maximum filling quantity, as long as the main float body functions correctly.

This limiting of the maximum filling quantity is important first and foremost in humidification devices for respiratory devices for artificial ventilation. Through such a humidification device, respiratory gas for the patient to be ventilated is to be humified, so that the respiratory gas is tolerable for the patient even under longer-lasting ventilation and sections of the physical respirator do not get dried out through excessively dry respiratory gas. In any case, however, fluid being carried away by the respiratory gas and reaching the patient's lung should be avoided in this process.

An excessively high filling level is not the only potential source of risk here for undesirable fluid transportation. A filling level which to begin with is correct can also create the risk of fluid transportation if the correct fluid quantity accumulates at the wrong location inside a humidification device. This can happen, for example, during tilting of the humidification device and with it the valve array. For one thing, the fluid quantity can thereby come close to an outlet aperture, which can promote transportation of fluid out of the humidification device. For another, through tilting of the valve array the buoyancy axis as the movement path component relevant for the movement of the float body between the sinking position and the buoyancy position is tilted away from the gravitational direction. As a consequence of this, the at least one float body, which thus far has been situated correctly in the buoyancy position can move away from it such that further fluid can flow into the filling volume although the correct maximum fluid quantity is already present in the humidification device.

SUMMARY OF THE INVENTION

It is, therefore, the task of the present invention to develop a valve array designed as described in the beginning in such a way that overfilling of a filling volume secured through the valve array with a fluid flowing through the duct can be prevented even in the case of a positional deviation of the valve array from a normal target operating position.

The present invention solves this task in the valve array mentioned at the beginning by having—when regarding the two float bodies in their respective sinking position as a reference state—the respective buoyancy volume sections of the two float bodies arranged with a separation from one another which is orthogonal to the buoyancy axis, where in a body separation region between the two buoyancy volume sections there is located at least one joint and/or where in a joint separation region between both joints there is located at least one buoyancy volume section.

Unless expressly stated otherwise, the operational state of the valve array in which the two float bodies are each in the sinking position is to be the reference state in which the present valve array will be described. The sinking position is here that position which a float body takes occupies in its container if the container is free from fluid.

The buoyancy axis is that straight axis along which a buoyancy force acts if a container carrying the valve array is supported in the normal operational state on a plane, horizontal, i.e. orthogonal to the gravitational direction ground. In the normal operational state, the buoyancy axis proceeds in parallel to the gravitational direction. If, however, the container exhibiting the valve array is tilted by a tilt angle with respect to its normal operational state by a tilt axis orthogonal to the gravitational direction, the buoyancy axis is inclined by the tilt angle relative to the gravitational direction.

The aforementioned reference state is always a normal operational state in which the buoyancy axis is parallel to the gravitational direction.

As for the rest, if it is stated that the valve body formation is lifted from the valve seat when the float bodies are in the sinking position, this should not rule out that the valve body formation is also lifted from the valve seat when the float bodies are in an intermediate position between the sinking position and the buoyancy position. In fact, in most cases the valve body formation will be lifted from the valve seat if no float body is in the buoyancy position.

Through the configuration of separation regions which in a general design of the present invention should be unbounded in their extension along the buoyancy axis, it is possible to arrange the two buoyancy volume sections in different spatial and planar regions, lying side by side orthogonally to the buoyancy axis, of the filling volume of a container accommodating the valve array. As a result of this arrangement at a spatial separation from one another, the float bodies, which so to speak act as sensors for detecting a filling level, can detect the filling height of a fluid filled in the filling volume in different regions of the filling volume lying with a separation from one another orthogonally to the buoyancy axis. Thus at least one of the buoyancy volume sections can be arranged off-center with respect to the filling volume arranged, such that in the normal operational state it can detect the filling height above the base of the filling volume and such that even in the tilted state of the container be displaced through an accumulation into the buoyancy position and thus close the duct for a passage of fluid.

The float bodies of the present valve array are, other than in the state of the art, not arranged hierarchically as main and reserve float body, but rather as float bodies on an equal footing. This is advantageous due to the arrangement described above of the buoyancy volume sections at a spatial separation from one another, since in this way each single float body, when sufficient fluid is accumulated in its arrangement region, rises into the buoyancy position and closes the duct.

'On an equal footing' means here that in the normal operational state the fluid quantity at which the first float body is displaced into the buoyancy position and the fluid quantity at which the second float body is displaced into the buoyancy position differ by no more than 10%, preferably by no more than 7.5% based on the larger of the two fluid quantities. Of course the two fluid quantities are amounts of an identical fluid.

In order to denote a section of a float body as belonging to the float body, the section is indicated in the present application by the same ordinal number as the float body whose section it forms. A first buoyancy volume section is therefore, for example, a buoyancy volume section of the first float body and the like.

In principle it can suffice if the joints and the buoyancy volume sections are arranged alternating consecutively with one another along a direction which encloses with the buoyancy axis a preferably right angle. Through this arrangement, a buoyancy volume section can for example capture the filling height of fluid in a central region lying nearer to the center of a filling volume and a further buoyancy volume section in an edge region lying nearer to the edge of the filling volume. A tilting of the valve array in either of two opposite tilt directions about a tilt axis can then advantageously lead to a closing of the duct, if in the reference state both joints are located in the body separation region. This makes possible the arrangement of the buoyancy volume sections of the float body at a quantitatively large separation from one another. The two buoyancy volume sections are then located on different sides of the joints and/or the joints between the buoyancy volume sections respectively.

For capturing the filling height and closing the duct when a filling height limit is exceeded in the normal operational state, the spatial arrangement of the buoyancy volume sections in directions orthogonal to the gravitational direction plays at best a subsidiary role compared with their spatial arrangement along the gravitational direction. For in the normal operational state, a fluid level of a fluid filled in the filling volume of a container accommodating the valve array proceeds orthogonally to the buoyancy axis. A shifting of a buoyancy volume section orthogonally to the buoyancy axis thus changes nothing in the buoyancy effected by the buoyancy volume section.

The tilt axis of a tilting to be captured especially reliably by the float bodies proceeds at a preferably right angle to the buoyancy axis through the separation region, which preferably is a body separation region.

Advantageously, at least one buoyancy volume section is arranged in a swiveling manner in such a way that a trajectory of its displacement between sinking position and buoyancy position, in the case of doubt its center of gravity trajectory, exhibits a predominant movement component proceeding in parallel to the buoyancy axis and only a subsidiary movement component which is orthogonal to the buoyancy axis. This can be realized by having at least one joint which is located in the body separation region arranged in a height extension region extending along the buoyancy axis, in which in the reference state at least one buoyancy volume section, preferably both buoyancy volume sections, also extend.

Preferably, in order to achieve the most uniform buoyancy forces possible with a filling quantity filled in the normal operational state, the buoyancy volume sections of both float bodies extend to at least 60% based on their volume in a common height extension region extending along the buoyancy axis, preferably completely in a common height extension region. For the same reasons, preferably the height dimensions of the two buoyancy volume sections differ in the reference state by no more than 10%, preferably by no more than 7.5%, based on the larger height dimension, especially preferably the height dimensions of the two buoyancy volume sections are identical in the reference state.

In principle, the two virtual swiveling axes about which the first and the second float body are articulated in a swiveling manner at their respective joints, can be arranged along the buoyancy axis with separation from one another. Advantageously little differing kinematics during a displacement between the sinking position and the buoyancy position with movement components that differ little from one another along the buoyancy axis on the one hand and orthogonally to it on the other, can be achieved by having a first virtual swivel axis about which the first float body is articulated in a swiveling manner at the first joint, and a second virtual swivel axis about which the second float body is articulated in a swiveling manner at the second joint, lying in a common virtual extension plane, where the virtual extension plane preferably intersects in the reference state at least one buoyancy volume section. The two virtual swiveling axes are preferably parallel to one another. The virtual swiveling axes are especially preferably arranged so close side by side relative to the separation from each buoyancy volume section along the buoyancy axis, that the plane spanned by the two swiveling axes intersects in the reference state both buoyancy volume sections.

An advantageously similar or even identical movement is performed by the two float bodies between their sinking position and their buoyancy position when the virtual extension plane is oriented orthogonally to the buoyancy axis. Since in the normal operational state the buoyancy axis proceeds in parallel to the gravitational direction, in this operational state a fluid level of a fluid filled in the filling volume of a container carrying the valve array is likewise orthogonal to the buoyancy axis.

In a preferably compact embodiment, the valve module can comprise a valve housing at which the duct is configured. The duct configured in the valve housing can be part of a longer line which can lead up to a fluid reservoir. Each joint comprises a float body-side joint section arranged or configured at the float body and a bearing-side joint section interacting with the float body-side joint section, arranged or configured at a swivel bearing. The bearing-side joint section can be configured at an arbitrary section of a container carrying the valve array. To facilitate the arrangement of the valve module as a preassembled module at or in a container, preferably the bearing-side joint section of at least one joint, preferably of both joints, is configured at the valve housing.

In principle, the valve housing can be built from several separately manufactured components. To facilitate fabrication and assembly, preferably the valve housing is configured in one or two parts, for instance through two half- or part-shells. For example, this is possible in an injection-molded valve housing even with a relatively complex component geometry.

Since the duct which is to be closed or released for a flow-through by the valve array exhibits a normally very small diameter dimension relative to the filling volume of the container accommodating the valve array, often the two float bodies have to act on the valve body formation in regions which spatially lie very near next to each other. This can be facilitated by the first buoyancy volume section being located nearer to the second swivel axis than to the first swivel axis and/or by the second buoyancy volume section being located nearer to the first swivel axis than to the second swivel axis.

Preferably at least one float body exhibits the buoyancy volume section, the float body-side joint section, and a connecting section which connects the buoyancy volume section with the float body-side joint section. For preferably the buoyancy volume section of at least one float body, preferably of both float bodies, is arranged with a separation from the swivel axis of the same float body arranged, so that the float body performs between the sinking position and the buoyancy position a movement path which is sufficient for a displacement of the valve body formation.

Such a connecting section can be a bridge formation. Thereby the buoyancy volume section can also be arranged at a distance from the joint of its float body in the filling volume, for instance at an edge region of same. More preferably, therefore, both float bodies are configured in the aforementioned manner. The two float bodies can therefore, as described above, be arranged in an entwined manner is such a way that their buoyancy volume sections in the reference state, and preferably also when the float bodies are situated in the buoyancy position, lie on different sides of the swiveling axes advantageously proceeding between them. Each buoyancy volume section is connected with its joint via the connecting section, where the swivel axis of the respective other buoyancy volume section lies nearer to the buoyancy volume section than its own swivel axis. Between the two swiveling axes, therefore, the connecting sections of the two float bodies overlap.

In principle, the float body can be coupled with the valve body formation via an arbitrary construction by means of a gear unit and/or push-rod unit and/or linkage unit, such that a movement of the float body into the buoyancy position effects a movement of the valve body formation into the closure position.

An especially simple but effective coupling of each float body with the valve body formation, which allows direct movement transmission from the float body, in particular from its connecting section, to the valve body formation, can be realized in a coupling region located between the two swiveling axes. Preferably, therefore, it is provided that a coupling of the first float body with the valve body formation is located in a coupling region between the first and the second swivel axis and/or that a coupling of the second float body with the valve body formation is located in a coupling region between the first and the second swivel axis. In case of doubt, the mentioned coupling region extends in parallel to the buoyancy axis and is bounded by two planes parallel to the buoyancy axis, of which each contains exactly one swivel axis.

Although in principle a coupling of the float body with the valve body formation can be designed as a coupling of the buoyancy volume section with the valve body formation, a coupling of the connecting section of the float body with the valve body formation is preferable since the connecting section is nearly freely configurable as regards its shape.

Advantageously on fabrication grounds, the first and the second float body can be configured identically. Then it suffices to fabricate only one float body, which solely through its arrangement at the valve array is a first or a second float body. Preferably the first and the second float body are arranged twisted about a transfer axis parallel to the buoyancy axis, in order to make sure that their buoyancy volume sections are each arranged in a different spatial region of the filling volume of the container carrying the valve array. Then through rotation about the transfer axis, where applicable also under additional displacement, the one float body can thus be virtually converted into the other. Alternatively, the float body can comprise a buoyancy volume section and a separate connecting section or consist of these components, where the connecting section is attachable to the buoyancy volume section and/or connectible with the buoyancy volume section, as the case may be. The float body can thus be built from at least the connecting section and the buoyancy volume section. This has the advantage that the connecting section can always be manufactured in the same form and can be rotated by 180 degrees about an axis for use for a second hollow body.

In a first possible embodiment, the valve seat formation can exhibit exactly one valve seat and the valve body formation can exhibit exactly one valve body, where the exactly one valve body can be brought into the closure position by each individual float body. Such a valve module is known for example from EP 2 119 466 A1, already mentioned above. In a second possible embodiment, the valve seat formation can comprise a first valve seat and with a separation from the latter a second valve seat, where both valve seats are penetrated through by the duct. Consequently, in this second embodiment the valve body formation comprises a first valve body and a second valve body movable relative to it. In this case, the first valve body is coupled with the first float body for common movement and can be brought into physical abutment against the first valve seat. Likewise, the second valve body is coupled with the second float body for common movement and can be brought into physical abutment against the second valve seat. A valve module designed in this manner is known from U.S. Pat. No. 5,445,143, already mentioned above. The first embodiment has the advantage of identical closure forces for both float bodies. The second embodiment has the advantage that each float body can be connected permanently with the valve body assigned to it.

The present invention also concerns a humidification device for a respiratory device, comprising a container with a filling volume, where the container exhibits an inlet aperture through which respiratory gas can be introduced into the filling volume, and exhibits an outlet aperture through which respiratory gas can be channeled out of the filling volume. The humidification device exhibits a valve array which is configured as described above. The duct of the valve array is here a supply duct for introducing fluid into the container.

The filling volume has consequently respiratory gas flowing through it and takes with it evaporated or vaporized fluid with an increase its humidity in the direction towards the patient. For better adjustability of the humidification of the respiratory gas in the filling volume, at least one wall section, preferably a bottom, of the container is made from a material with higher thermal conductivity than the rest of the container. Preferably the majority of the container wall is made from a synthetic. The wall section with higher thermal conductivity is preferably made from metal. The wall section with higher thermal conductivity can thus be brought into heat-transferring contact with a preferably output-controllable heat source, such that through the heat source by means of the wall section with higher thermal conductivity heat can be brought into the fluid in the filling volume and thus the temporal evaporation rate of this fluid quantitatively changed.

The container exhibits a container bottom and a side-wall arrangement sticking out from the container bottom. For a desired closure of the duct in the event of undesired tilting of the container, it is advantageous if at least one buoyancy volume section is arranged nearer to the side-wall arrangement than in a central region of the filling volume of the container, since in the event of tilting of the container, fluid filled in the filling volume normally accumulates in an edge region near the side-wall arrangement. Therefore preferably it is the case for at least one, preferably for both float bodies that the separation of the buoyancy volume section of the one float body from the section of the side-wall arrangement located next to it is smaller than the separation from the buoyancy volume section of the respective other float body.

Preferably a substantial part of the filling volume of the container is available for the flow-through with respiratory gas and for the mixing of the flowing respiratory gas with evaporated and/or vaporized fluid respectively. Therefore preferably the volume taken up by the two float bodies comes to no more than 20%, preferably no more than 15% of the filling volume of the container.

As already explicated above, preferably the two float bodies are functionally equivalent, which is manifested in the humidification device by the fact that in normal use with a buoyancy axis oriented in parallel to the gravitational direction, the first and the second float body are configured and arranged in such a way that when using demineralized water at a temperature of 20° C. as a reference fluid for filling the container, the filling quantity which is needed for the first floating body to reach its buoyancy position differs from the filling quantity which is needed for the second float body to reach its buoyancy position by no more than 10%, preferably by no more than 5%, based on the larger of the two filling quantities.

These and other objects, aspects, features and advantages of the invention will become apparent to those skilled in the art upon a reading of the Detailed Description of the invention set forth below taken together with the drawings which will be described in the next section.

BRIEF DESCRIPTION OF THE DRAWINGS

The invention may take physical form in certain parts and arrangement of parts, a preferred embodiment of which will be described in detail and illustrated in the accompanying drawings which forms a part hereof and wherein.

DESCRIPTION OF PREFERRED EMBODIMENTS

Figure 1:
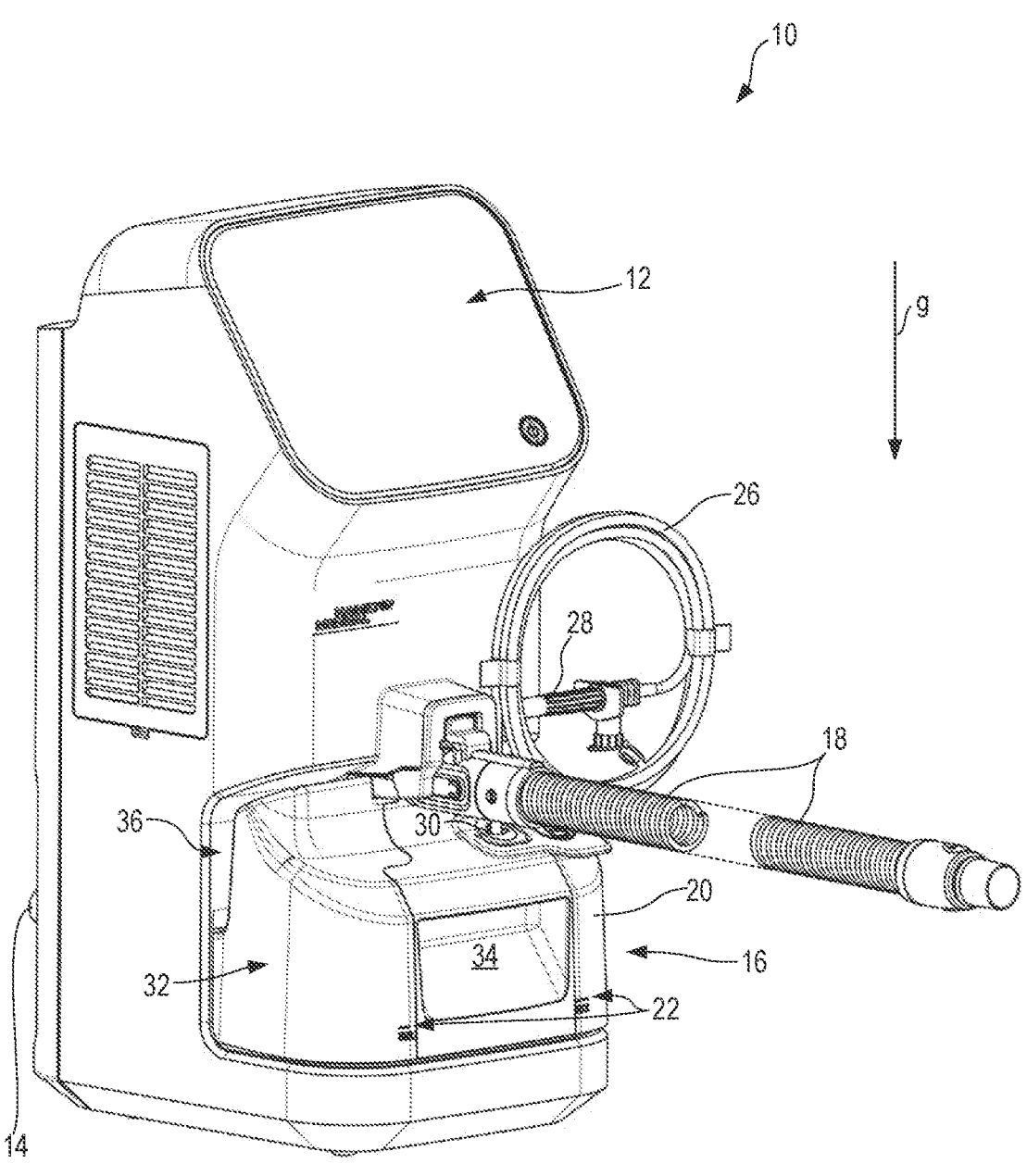
FIG. 1: A rough schematic perspective view of a respiratory device with an embodiment according to the invention of a humidification device.

Referring now to the drawings wherein the showings are for the purpose of illustrating preferred and alternative embodiments of the invention only and not for the purpose of limiting the same, in FIG. 1, a respiratory device is labelled generally by 10. The respiratory device 10 exhibits a touchscreen 12 as an input/output device, which is connected for data transmission with a control device arranged in the housing of the respiratory device 10. The respiratory device 10 exhibits in its housing a fan, with which ambient air is aspirated as a respiratory gas via an inlet 14 on the back. Alternatively, however, the respiratory gas can also be mixed out of various gases which are connected with the respiratory device by means of connectors.

In the lower front half of the respiratory device 10 there is arranged a humidification device 16 which serves for the humidification of the respiratory gas before it is conveyed towards a patient via a ventilation tube 18.

The humidification device 16 comprises a container 20, in which fluid, normally water, can be filled. The fluid filled in the container 20 evaporates and/or vaporizes respectively where the respiratory gas flowing through the container 20 mixes with the evaporated and/or vaporized fluid respectively. Thereby the respiratory gas leaves the container 20 through the ventilation tube 18 with a quantitatively higher absolute humidity than it was conveyed into the container 20. The ventilation tube 18 is depicted shortened in FIG. 1 only with its two longitudinal end sections. A middle section of the ventilation tube 18 is not depicted.

In FIG. 1 the respiratory device 10 and with it the humidification device 16 is in a normal operational state, in which a flat setting-up surface of the respiratory device 10 is oriented orthogonally to the gravitational direction g.

A marking 22 on the front of the container 20 indicates the maximum filling level which the fluid in the filling volume 24 (see FIG. 3) of the container 20 should not exceed.

Fluid from a reservoir not depicted in FIG. 1 can be introduced into the filling volume 24 of the container 20 via a supply line 26. The supply line 26 is depicted in FIG. 1 not in use, by way of example as a tube roll. The supply line 26 exhibits at its longitudinal end which is remote from the container 20 a coupling formation 28, for example a pierce coupling 28, with which the lumen of the supply line 26 can be connected with a stocked fluid. The coupling formation 28 allows in a way which is known per se the admixture of additives, such as for instance drugs, to the fluid flowing in the supply line 26.

The supply line 26 is coupled at its longitudinal end which is near to the container 20 with a passage opening 30 in the container wall 32, such that fluid flowing from the fluid reservoir through the supply line 26, normally gravity-driven, can reach the filling volume 24 of the container 20.

Via a recessed handle 34 at the front of the container 20, the container 20 can be removed from an insert recess 36 in the respiratory device 10 and inserted back into it.

Figure 3:
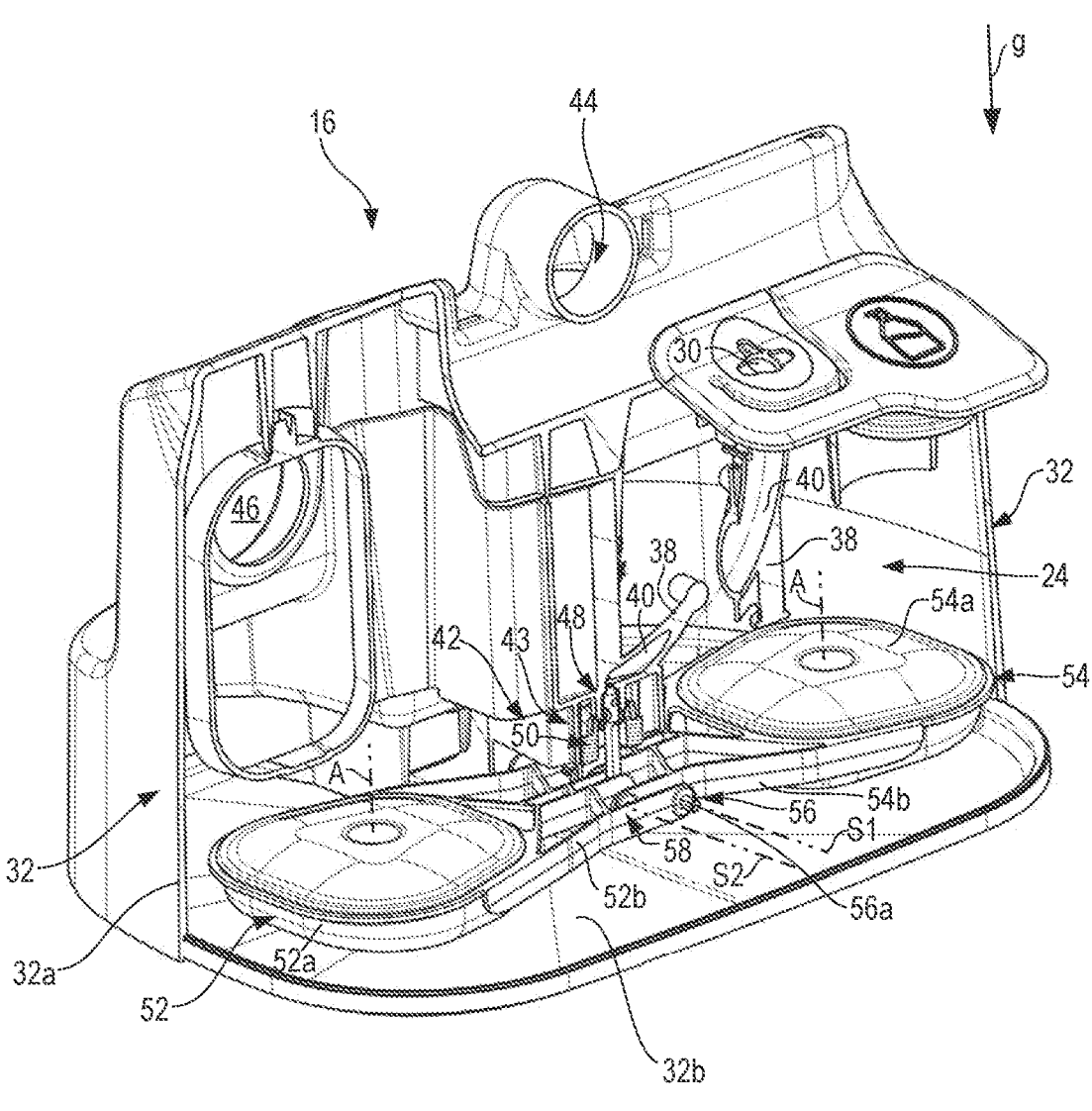

As FIG. 3 shows, there connects on the inside of the container wall 32 at the passage opening 30 a duct component 38, in which a duct 40 is configured which conveys the fluid supplied by the supply line 26 to a valve array 42 and, depending on the operational state of the valve array 42, through the latter. The duct component 38 is depicted in FIG. 3 cut along a sectional plane parallel to the buoyancy axis A and orthogonal to the swiveling axes S1 and S2 elucidated further below, in order to show the duct 40. In a middle region of the duct component 38, a piece is cut out of it due to its curvature about an axis of curvature parallel to the buoyancy axis A.

Figure 2:
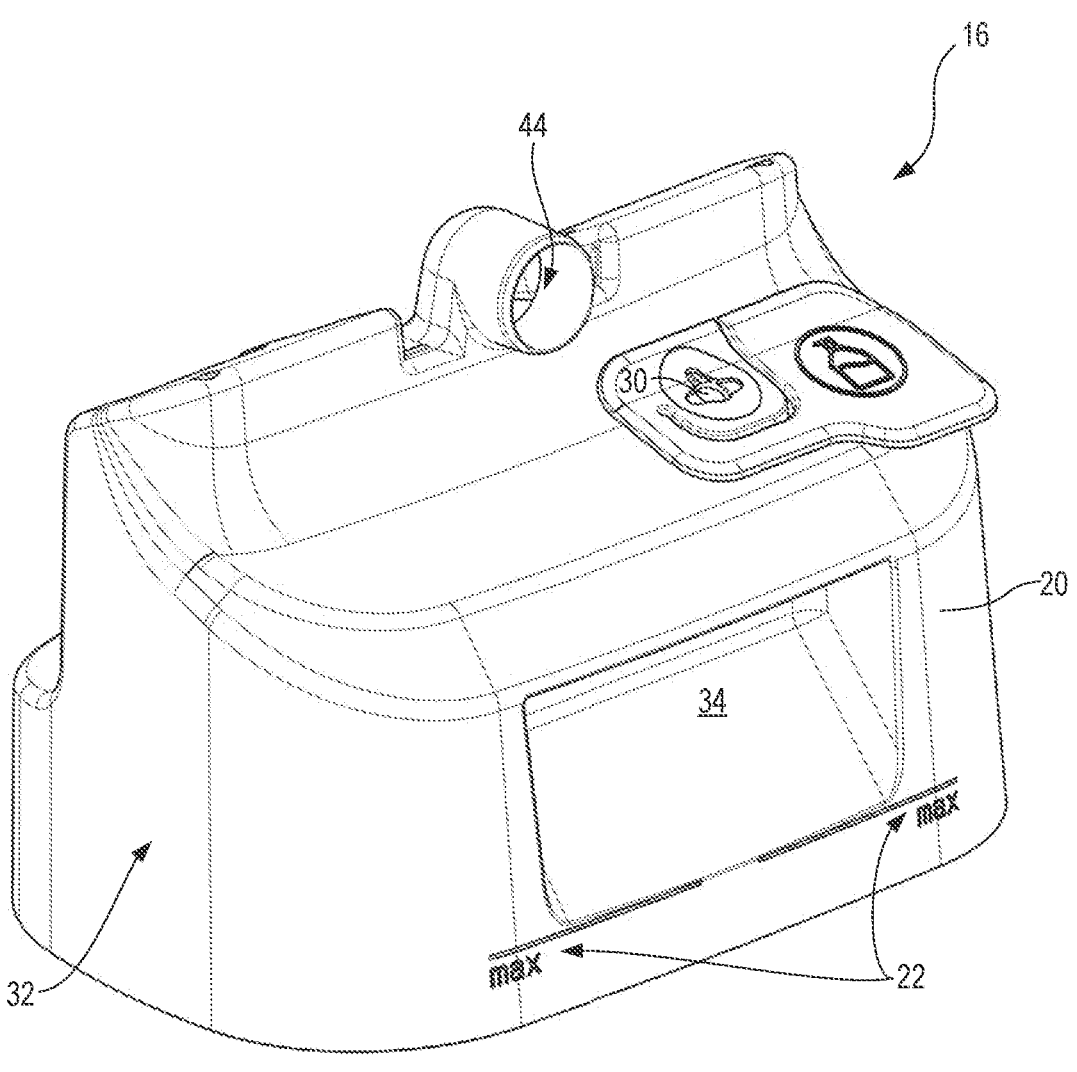
FIG. 2: A rough schematic perspective view of the humidification device of FIG. 1, FIG. 3: The humidification device of FIG. 2 with partly cut-away side-wall arrangement and partly cut-away valve module.

In FIGS. 2 and 3 there is besides depicted the outlet aperture 44, through which the respiratory gas flowing through the filling volume 24 emerges from the container 20. FIG. 3 shows the inlet aperture 46, through which the respiratory gas flows into the filling volume 24.

The container wall 32 comprises a side-wall arrangement 32*a* and an essentially planar bottom 32*b*. The side-wall arrangement 32*a* is preferably molded from a thermoplastic synthetic in an injection molding process. The bottom 32*b* is made from metal and exhibits a higher thermal conductivity than in the side-wall arrangement 32*a*. The insert recess 36 of the respiratory device 10 exhibits at its underside a heating device, which when the humidification device 16 is inserted in the insert recess 36 is in heat-transmitting contact with the preferably metallic bottom 32*b* in order to input heat with the shortest possible time delay and with the smallest possible losses into the fluid which in the operational reference state accumulates at the bottom 32*b*. In the operational reference state of the humidification device 16, the bottom 32*b* of the container 20 is oriented essentially orthogonally to the gravitational direction g, such that a fluid level of a fluid which is filled in the filling volume 24 is aligned essentially in parallel to the bottom 32*b*.

The valve array 42 comprises a valve module 43 with a valve seat formation 48 penetrated through by the duct 40 and with a valve body formation 50 which is moveable relative to the valve seat formation 48 and which interacts with the valve seat formation 48 in order to electively close or open the duct which penetrates through the valve seat formation 48.

In the normal operational state the duct 40 penetrates through the valve seat formation 48 in parallel to the gravitational direction g, which is why preferably the valve body formation 50 is likewise moveable relative to the valve seat formation 48 in parallel to the gravitational direction g. In principle, preferably the valve body formation 50 is moveable relative to the valve seat formation 48 in parallel to the direction in which the duct 40 penetrates through the valve seat formation 48.

Figure 6:
FIG. 6: The humidification device of FIGS. 2 and 3 when observed from below with the bottom of the device omitted.

The valve array 42 exhibits as actuators of the valve body formation 50 a first float body 52 and a second float body 54. The two float bodies 52 and 54 are configured identically and are merely arranged so as to be oriented differently in the filling volume 24. The two float bodies are convertible to each other in a virtual manner through rotation by 180° about a transfer axis Ub which is orthogonal to the bottom 32*b* (see FIG. 6).

The first float body 52 is mounted in an articulated manner at a first joint 56 about a first swivel axis S1. The first float body 52 exhibits with a separation from the first swivel axis S1 a buoyancy volume section 52*a*, which is connected with the joint 56 via a connecting section 52*b*. The connecting section 52*b* is configured as a framework-like bridge section. The buoyancy volume section 52*a* occupies the main volume of the first float body 52 and in interaction with a fluid accommodated in the filling volume 24 makes for the greatest part of the buoyancy provided by the first float body 52. The buoyancy volume section 52*a* moves between its operating positions depicted in FIGS. 4 and 5: buoyancy position (FIG. 4) and sinking position (FIG. 5), along a buoyancy axis A which in the normal operational state of the valve array 42 proceeds in parallel to the gravitational direction g. Since the buoyancy volume section 52*a* really unavoidably executes a circular path about the first swivel axis S1, the trajectory of the buoyancy volume section 52*a* also exhibits between its operating positions a movement component orthogonal to the buoyancy axis A, which however in the first place does not contribute to the displacement of the valve body formation and which in the second place is quantitatively negligibly small in comparison with the movement component along the buoyancy axis A.

As can be clearly discerned in FIG. 3, the first buoyancy volume section 52*a* lies close to the section of the side-wall arrangement 32*a* which is nearest to it. The first buoyancy volume section 52*a* lies closer to the section of the side-wall arrangement 32*a* which is nearest to it than to a perpendicular bisector penetrating through the bottom 32*b* at its centroid of area, which proceeds orthogonally to the bottom 32*b* and thereby parallel to the buoyancy axis A. The perpendicular bisector proceeds in FIG. 3 in a plane parallel to the buoyancy axis A lying at the middle of the separation between the first swivel axis S1 and the second swivel axis S2. More particularly, each buoyancy volume section 52*a* and 54*a* is situated respectively closer to the section of the side-wall arrangement 32*a* which is nearest to it than to the respective other buoyancy volume section 52*a* or 54*a*, as the case may be.

The second float body 54 is swivel-mounted about the second swivel axis S2 in an analogous manner to the first float body 54 about the first swivel axis S1. Because of the identical configuration, the second float body 54 exhibits a buoyancy volume section 54*a* which is connected with a second joint 58 through a connecting section 54*b* configured as a framework-like bridge formation. "Framework-like" means in this context that the bridge formation exhibits longitudinal and transverse struts connected with one another. In order to achieve a statically stable bridge formation, the longitudinal and transverse struts form either triangle or square frameworks.

Figure 4:
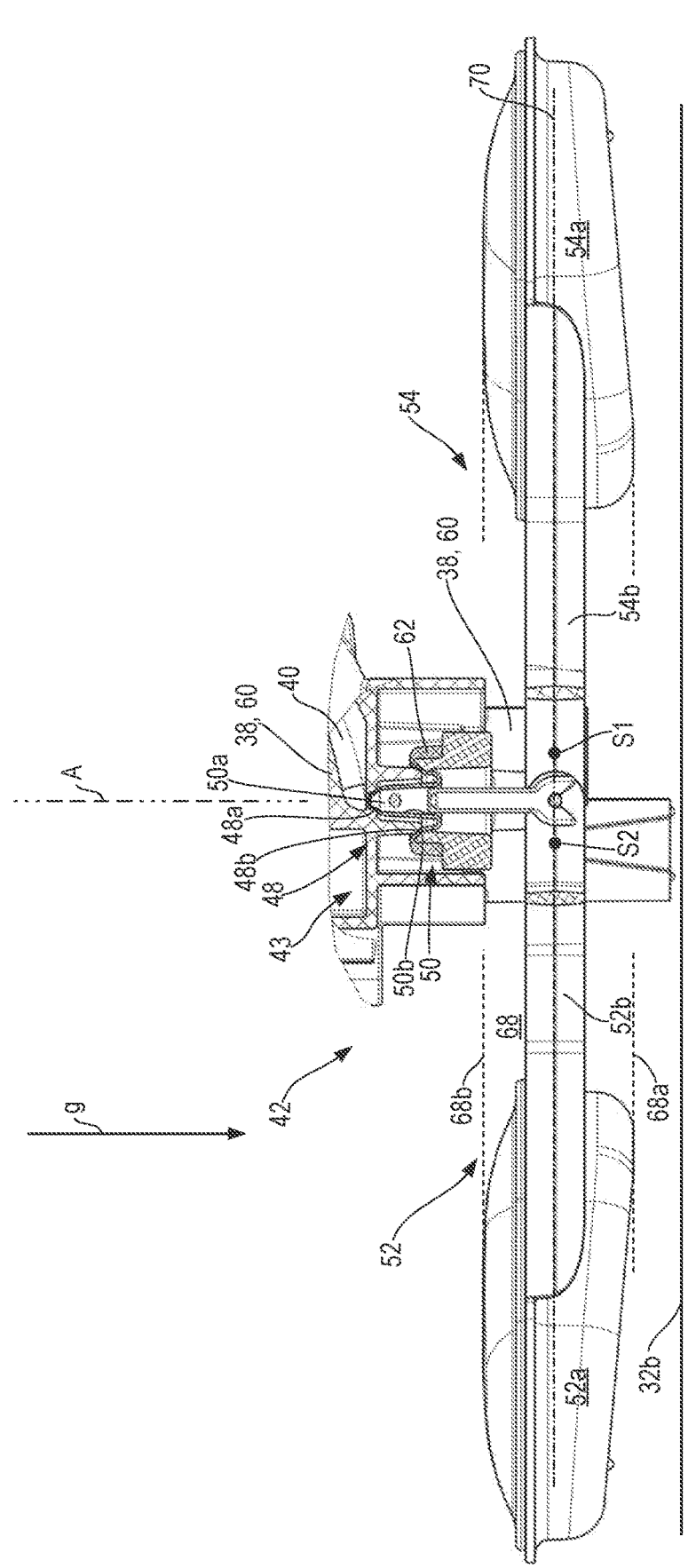
FIG. 4: An embodiment according to the invention of a valve array of the present application, as used for example in the humidification device of FIGS. 2 and 3, with each of the float bodies in the buoyancy position.

The structure of the valve module 43 is elucidated in further detail by reference to FIG. 4. The valve seat formation 48 exhibits a first valve seat 48*a* and a second valve seat 48*b* configured along the buoyancy axis A with a separation from the latter. The two valve seats 48*a* and 48*b* are configured at the duct component 38, which also forms a valve housing 60. The first valve seat 48*a* exhibits by way of example a negative conical abutment surface, the second valve seat 48*b* a positive conical abutment surface. Both valve seats 48*a* and 48*b* are penetrated through by the duct 40.

The valve body formation 50 exhibits a first valve body 50*a*, which in the depicted example is configured as pin-shaped, and exhibits a second valve body 50*b* moveable relative to the former, which in the depicted example is configured as tube-shaped. The first valve body 50*a* exhibits a positive conical abutment surface for interacting with the negative conical abutment surface of the first valve seat 48*a*. The second valve body 50*b* exhibits a negative conical abutment surface for interacting with the positive conical abutment surface of the second valve seat 48*b*. The valve body formation 50 exhibits besides a soft-elastic membrane 62, which in order to increase the imperviousness of the valve module 43 in the closure position shown in FIG. 4 spans both valve bodies 50*a* and 50*b*. Both valve bodies 50*a* and 50*b* are predominantly displaceable along the buoyancy axis A.

Figure 5:
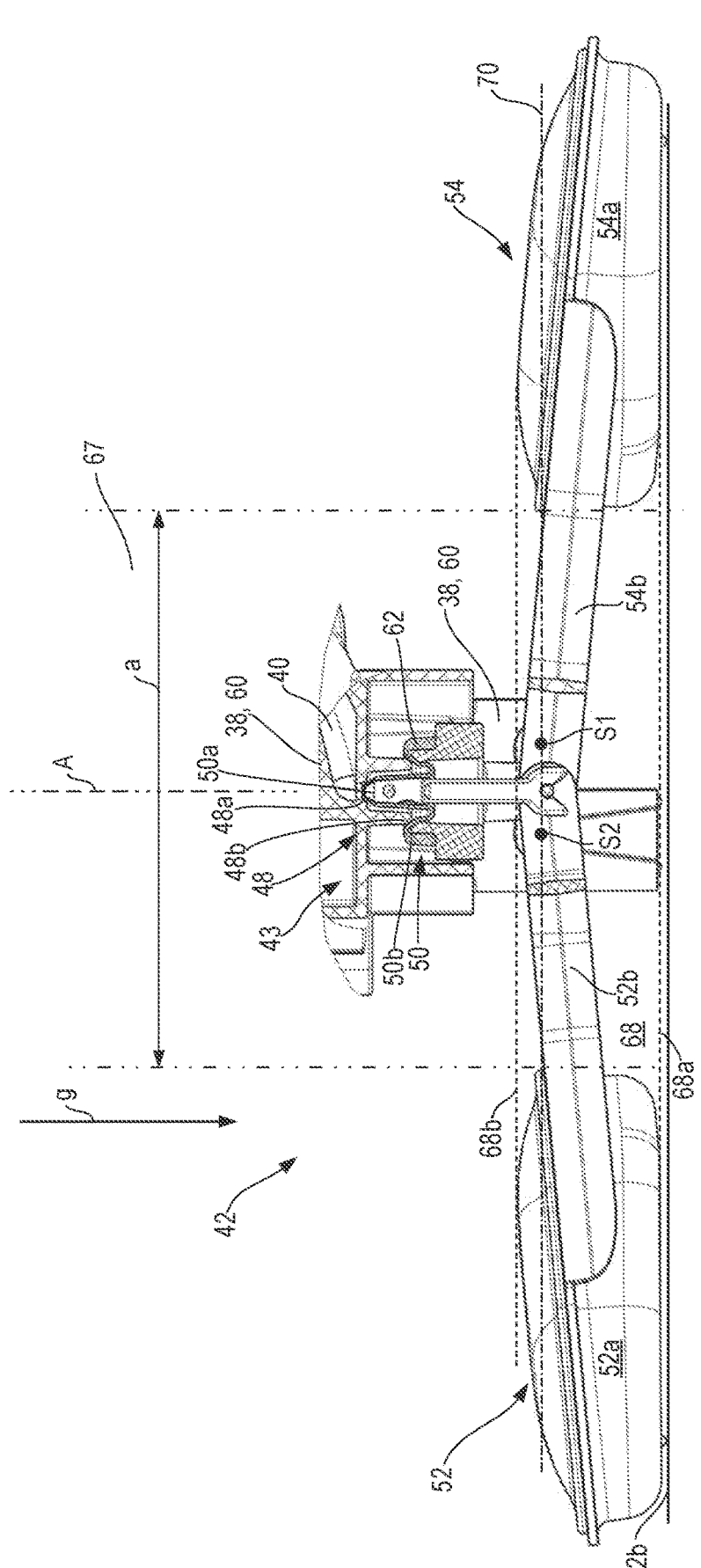
FIG. 5: The valve array of FIG. 4 in the sinking position as reference state.

The first valve body 50*a* is coupled in an articulated manner with the first float body 52, in the depicted example with its connecting section 52*b*, such that a movement of the first connecting section 52*b* along the buoyancy axis A effects a displacement of the first valve body 50*a* between the closure position shown in FIG. 4 and the passage position shown in FIG. 5.

The second valve body 50*b* is likewise coupled in an articulated manner with the second float body 54, in the depicted example with its connecting section 54*b*, such that a movement of the second connecting section 54*b* along the buoyancy axis A effects a displacement of the second valve body 50*b* between the closure position shown in FIG. 4 and the passage position shown in FIG. 5. In this process it is sufficient if one of the two valve body 50*a* or 50*b* is displaced into its closure position for the duct 40 to be closed to a fluid through-flow.

The valve array 42 is designed in such a way that the joint axes 64 and 66 of the connections (see FIG. 6) of the first valve body 50*a* with the first connecting section 52*b* and/or of the second valve body 50*b* with the second connecting section 54*b* respectively proceed coaxially when each float body 52 and 54 is situated in at least one identical end position out of sinking position and buoyancy position. The coaxial joint axes 64 and 66 are then arranged equidistantly to the swiveling axes S1 and S2.

The valve array 42 is further designed in such a way that the float bodies 52 and 54 are arranged essentially diametrically to the parallel buoyancy axis (A). In other words: when the joint axes 64 and 66 span a virtual reference plane parallel to the buoyancy axis (A), one float body is situated on one side of the virtual reference plane and the other float body on the other side of the virtual reference plane.

Out of the buoyancy volume sections 52*a* and 54*a* arranged with a separation a (see FIG. 5) from one another, the first buoyancy volume section 52*a* lies nearer to the second swivel axis S2 and the second buoyancy volume section 54*a* lies nearer to the first swivel axis S1. The coupling points of the two valve body 50*a* and 50*b* with the float bodies 52 and 54 lie in the extension region of the two connecting sections 52*b* and 54*b*, which is located between the two swiveling axes S1 and S2.

The joints 56 and 58 are formed between the float bodies 52 and 54 respectively and the valve housing 60. In the depicted example there is configured at the float bodies 52 and 54 respectively as injection-molded components a stub shaft as a float body-side joint section (see stub shaft 56*a* in FIG. 3 and the stub shafts 56*a* and 58*a* in FIG. 6). In the valve housing 60 there is configured as a bearing-side joint section a recess which accommodates the respective stub shaft.

In FIG. 5, the valve array 42 is depicted in its sinking position and hence in the reference state used in the descriptive introduction for its elucidation. The buoyancy volume sections 52*a* and 54*a* exhibit on the outside of their bottoms small projections, with which the buoyancy volume sections 52*a* and 54*a* rest on the preferably flat bottom 32*b* of the container 20. The small projections ensure that the buoyancy volume sections 52*a* and 54*a* can be underwashed by fluid in the filling volume 24 even in the sinking position, such that even the smallest fluid quantities effect buoyancy at the buoyancy volume sections 52*a* and 54*a*.

Between the buoyancy volume sections 52*a* and 54*a* there is situated a body separation region 67, in which in the depicted embodiment example both joints 56 and 58 are arranged. The body separation region 67 extends orthogonally to the buoyancy axis A beyond the separation a which exists between the buoyancy volume sections 52*a* and 54*a*. Through the arrangement of the buoyancy volume sections 52*a* and 54*a* with a separation a from one another, each buoyancy volume section 52*a* and 54*a* can be arranged at an edge region of the filling volume 24, i.e. near a section of the side-wall arrangement 32*a*, which considerably increases in an advantageous manner the sensitivity of the valve array 42 to a tilting of the humidification device 16 about a tilt axis which is orthogonal both to the buoyancy axis A and to the direction of the separation a.

When both float bodies are in the sinking position, the joints 56 and 58 and the swiveling axes S1 and S2 defined by them are situated in a common height extension region 68 of the buoyancy volume sections 52*a* and 54*a* which is bounded below by a plane 68*a* and above by a plane 68*b*. The two planes 68*a* and 68*b* are osculating planes orthogonal to the buoyancy axis A at the undersides and the topsides respectively of the buoyancy volume sections 52*a* and 54*a*. This arrangement of joints 56 and 58 relative to the buoyancy volume sections 52*a* and 54*a* positively driven by them makes for advantageous kinematics of the buoyancy volume sections 52*a* and 54*a* with a significantly larger movement component along the buoyancy axis A than orthogonally to it. For the same reason of achieving an advantageous kinematics of the buoyancy volume sections 52*a* and 54*a*, the swiveling axes S1 and S2 are arranged in a common virtual plane 70 which intersects the buoyancy volume sections 52*a* and 54*a* at least when these are in the sinking position. As FIG. 4 shows, however, this is also the case when the buoyancy volume sections 52*a* and 54*a* are in the buoyancy position. The virtual extension plane 70 is oriented orthogonally to the buoyancy axis A and hence orthogonally to the drawing plane of FIGS. 4 and 5.

Since the individual height extension regions of the two buoyancy volume sections 52*a* and 54*a* are identical regarding dimension and position, exactly two planes, an upper and a lower, suffice for determining the common height extension region 68 which is identical with the individual height extension regions. If the individual height extension regions of the two buoyancy volume sections 52*a* and 54*a* differ regarding dimension and/or position, then the individual height extension regions of each buoyancy volume section 52*a* and 54*a* have to be determined analogously. The common height extension region 68 is the intersection set of the individual height extension regions.

When the humidification device 16 and hence the valve array 42 is tilted in an arbitrary tilt direction about a tilt axis parallel to the swiveling axes S1 and S2, fluid is displaced towards the side-wall section lowered by the tilt movements, whereby fluid accumulates in an arrangement region of one of the two buoyancy volume sections 52*a* and 54*a* and thus can displace the relevant buoyancy volume section and with it the entire float body into the buoyancy position. Hereby fluid can be prevented from flowing on into the filling volume of the humidification device 16 when the latter is in an undesirably tilted position. This also applies to a tilt movement about a tilt axis which is not completely parallel to one of the swiveling axes, as long as its course component along one of the swiveling axes is greater than orthogonally to it.

The depiction in the embodiment example notwithstanding, the swiveling axes S1 and S2 do not have to be parallel to another. Preferably, however, they lie in the same plane.

While considerable emphasis has been placed on the preferred embodiments of the invention illustrated and described herein, it will be appreciated that other embodiments, and equivalences thereof, can be made and that many changes can be made in the preferred embodiments without departing from the principles of the invention. Furthermore, the embodiments described above can be combined to form yet other embodiments of the invention of this application. Accordingly, it is to be distinctly understood that the foregoing descriptive matter is to be interpreted merely as illustrative of the invention and not as a limitation.

The invention claimed is:

1. A float-controlled valve array, comprising a valve module with a duct, a valve seat formation penetrated through by the duct, and a valve body formation, where the valve body formation is displaceable relative to the valve seat formation between a closure position in which the duct is closed through physical abutment of the valve body formation against the valve seat formation, and a passage position in which the valve body formation is arranged with a separation from the valve seat formation such that flow through the duct is possible, where the valve array further comprises a first float body with a first buoyancy volume section and a second float body with a second buoyancy volume section, where the first float body is articulated in a swiveling manner at a first joint and where the second float body is articulated in a swiveling manner at a second joint such that in normal operation each float body is moveable along a buoyancy axis parallel to the gravitational direction between a sinking position and a buoyancy position, where the first and the second float body is each coupled in such a way with the valve body formation that the valve body formation is in the closure position when at least one of the float bodies is in the buoyancy position, and is in the passage position when both float bodies are in the sinking position, wherein when regarding the two float bodies in their respective sinking position as a reference state, the respective buoyancy volume sections of the two float bodies are arranged with separation from one another which is orthogonal to the buoyancy axis, where in a body separation region between the two buoyancy volume sections there is located at least one joint.

2. The valve array according to claim 1, wherein in the reference state both joints are located in the body separation region between the two buoyancy volume sections.

3. The valve array according to claim 1, wherein at least one joint located in the body separation region is arranged in a height extension region extending along the buoyancy axis, in which in the reference state there also extend the two buoyancy volume sections.

4. The valve array according to claim 1, wherein a first virtual swivel axis about which the first float body is articulated in a swiveling manner at the first joint and a second virtual swivel axis about which the second float body is articulated in a swiveling manner at the second joint lie in a common virtual extension plane.

5. The valve array according to claim 4, wherein in the reference state the virtual extension plane intersects a buoyancy volume section of the first and of the second float body.

6. The valve array according to claim 4, wherein the virtual extension plane is oriented orthogonally to the buoyancy axis.

7. The valve array according to claim 1, wherein the valve module comprises a valve housing at which the duct is configured.

8. The valve array according to claim 4, wherein the first buoyancy volume section lies closer to the second virtual swivel axis than to the first virtual swivel axis and/or that the second buoyancy volume section lies closer to the first virtual swivel axis than to the second virtual swivel axis.

9. The valve array according to claim 8, wherein a coupling of the first float body with the valve body formation lies in a region between the first and the second swivel axis and/or that a coupling of the second float body with the valve body formation lies in a region between the first and the second swivel axis.

10. The valve array according to claim 1, wherein the first and the second float body are configured identically.

11. The valve array according to claim 1, wherein the valve seat formation comprises a first valve seat and a second valve seat with a separation from the former, where both valve seats are penetrated through by the duct, and that the valve body formation comprises a first valve body and a second valve body moveable relative to it, where the first valve body is coupled with the first float body for common movement and configured to be brought into physical abutment against the first valve seat, and where the second valve body is coupled with the second float body for common movement and configured to be brought into physical abutment against the second valve seat.

12. A humidification device for a respiratory device, comprising a container with a filling volume, where the container exhibits an inlet aperture through which respiratory gas is introduced into the filling volume, and exhibits an outlet aperture through which respiratory gas is channeled out of the filling volume, where the humidification device includes a valve array according to claim 1, where the duct of the valve array is a supply duct for introducing fluid into the container.

13. The humidification device according to claim 12, wherein the container exhibits a container bottom and a side-wall arrangement sticking out from the container bottom, where for at least one of the float bodies the separation of its buoyancy volume section from the section of the side-wall arrangement located next to it is smaller than the separation from the buoyancy volume section of the respective other float body.

14. The humidification device according to claim 12, wherein the container exhibits a container bottom and a side-wall arrangement sticking out from the container bottom, wherein for both of the float bodies the separation of its buoyancy volume section from the section of the side-wall arrangement located next to it is smaller than the separation from the buoyancy volume section of the respective other float body.

15. The humidification device according to claim 12, wherein the volume taken up by the two float bodies comes to no more than 20% of the filling volume of the container.

16. The humidification device according to claim 13, wherein the volume taken up by the two float bodies comes to no more than 15% of the filling volume of the container.

17. The humidification device according to claim 12, wherein in normal use with a buoyancy axis oriented in parallel to the gravitational direction, the first and the second float body are configured and arranged in such a way that when using demineralized water at a temperature of 20° C. as a reference fluid for filling the container, the filling quantity which is needed for the first float body to reach its buoyancy position differs from the filling quantity which is needed for the second float body to reach its buoyancy position by no more than 10% based on the larger of the two filling quantities.

18. The humidification device according to claim 15, wherein in normal use with a buoyancy axis oriented in parallel to the gravitational direction, the first and the second float body are configured and arranged in such a way that when using demineralized water at a temperature of 20° C. as a reference fluid for filling the container, the filling quantity which is needed for the first float body to reach its buoyancy position differs from the filling quantity which is needed for the second float body to reach its buoyancy position by no more than 5% based on the larger of the two filling quantities.

19. The humidification device according to claim 2, wherein the first float body is articulated about a first swiveling axis at a first joint, the second float body is articulated about a second swiveling axis at a second joint, wherein the first and the second swiveling axes proceed between the first and the second float body.

* * * * *